United States Patent [19]

Halberstadt et al.

[11] Patent Number: 5,681,587

[45] Date of Patent: *Oct. 28, 1997

[54] GROWTH OF ADULT PANCREATIC ISLET CELLS

[75] Inventors: Craig Halberstadt, San Diego, Calif.; Michael Zimber, Pullman, Wash.; John J. Grzesiak, Cardiff, Calif.

[73] Assignee: Desmos, Inc., San Diego, Calif.

[*] Notice: The portion of the term of this patent subsequent to Mar. 29, 2016, has been disclaimed.

[21] Appl. No.: 626,394

[22] Filed: Mar. 29, 1996

Related U.S. Application Data

[60] Provisional application No. 60/004,878 Oct. 6, 1995.

[51] Int. Cl.[6] .................... A61K 35/39; A61K 38/28; C12N 5/06; C12N 5/08
[52] U.S. Cl. .................... 424/562; 424/556; 424/572; 435/350; 435/351; 435/352; 435/363; 435/366; 435/395; 435/402; 514/3; 514/4
[58] Field of Search .................... 424/520, 550, 424/556, 562, 572; 435/240.2, 240.21, 240.23, 350, 351, 352, 363, 366, 395, 402; 514/3, 4

[56] References Cited

U.S. PATENT DOCUMENTS 5,422,264 6/1995 Quaranta et al. .
5,510,263 4/1996 Quaranta et al. .

FOREIGN PATENT DOCUMENTS

WO 92/17498 10/1992 WIPO .
WO 94/05316 3/1994 WIPO .
WO 94/23016 10/1994 WIPO .
WO 95/06660 3/1995 WIPO .
WO 95/13103 5/1995 WIPO .
WO 95/29988 11/1995 WIPO .

OTHER PUBLICATIONS

Maes, E. and Pipeleers, D. Endocrinolgy. 114(6): 2205–2209, Jun. 1994.
Dahl, G. and Gratzl, M. Cytobiologie. 12(2): 344–355, Feb. 1976.
N. Kaiser, "Monolayer Culture of Adult Rat Pancreatic Islets on Extracellular Matrix: Long Term Maintenance of Differentiated B–Cell Function", *Endocrinology* 123(2):834–840 (1988).
C. Lucas–Clerc, et al., "Long–term culture of human pancreatic islets in an extracellular matrix: morphological and metabolic effects", *Molecular and Cellular Endocrinology* 94:9–20 (1993).
A. Hayek, et al. (1985) "Growth Factor/Matrix–Induced Proliferation of Human Adult B–Cells" *Diabetes* 44:1458–1460.
W.G. Carter, et al. (1991) "Epiligrin, A New Cell Adhesion Ligand for Integrin α3β1 in Epithelial Basement Membranes", *Cell*, 65:599–610.

B. Hsi, et al. (1987) "Monoclonal Antibody $GB_36$ Raised Against Human Trophoblast Recognizes a Novel Epithelial Antigen", *Placenta*, 8:209–217.
H. Iwata, et al. (1994) "Feasibilty of Agarose Microbeads with Xenogeneic Islets as a Bioartificial Pancreas", *Journal of Biomedical Materials Research*, 28:1003–1011.
K. Izumi, et al. (1981) "In Vitro Induction of Ornithine Decarboxylase in Urinary Bladder Carcinoma Cells", *Cancer Research*, 41:405–409.
K. Kover et al. (1989) "Development of a Method for Isolation of Islets from Human Fetal Pancreas", *Diabetes*, 38:917–924.
R.P. Lanza, et al. (1993) "Biohybrid Artificial Pancreas", *Transplantation*, 56(5):1067–1072.
F.N. Leach, et al. (1973) "Insulin Release from Human Foetal Pancreas in Tissue Culture", *J. Endocr.*, 59:65–79.
T. Otonkoski, et al. (1988) "Morphology, Yield and Functional Integrity of Islet–Like Cell Clusters in Tissue Culture of Human Fetal Pancreata Obtained After Different Means of Abortion", *Acta Endocrinologica*, 118:68–76.
P. Rousselle, et al. (1991) "Kalinin: An Epithelium–Specific Basement Membrane Adhesion Molecule that is a Component of Anchoring Filaments", *The Journal of Cell Biology*, 114(3):567–576.
P. Rousselle, et al. (1994) "Kalinin is More Efficient Than Laminin in Promoting Adhesion of Primary Keratinocytes and Some Other Epithelial Cells and has a Different Requirement for Integrin Receptors", *The Journal of Cell Biology*, 125(1):205–214.
S. Sandler, et al. (1985) "Tissue Culture of Human Fetal Pancreas", *Diabetes*, 34:1113–1119.
A.M. Simpson, et al. (1991) "Characterization of Endocrine–Rich Monolayers of Human Fetal Pancreas that Display Reduced Immunogenicity", *Diabetes*, 40:800–808.
H.D. Soule, et al. (1990) "Isolation and Characterization of a Spontaneously Immortalized Human Breast Epithelial Cell Line, MCF–10", *Cancer Research*, 50:6075–6086.
L. Tait, et al. (1990) "Ultrastructural and Immunocytochemical Characterization of an Immortalized Human Breast Epithelial Cell Line, MCF–10", *Cancer Research*, 50:6087–6094.
P. Verrando, et al. (1988) "The New Basement Membrane Antigen Recognized by the Monoclonal Antibody GB3 is a Large Size Glycoprotein: Modulation of Its Expression by Retinoic Acid", *Biochimica et Biophysica Acta*, 942:45–56.
F. Voss, et al. (1989) "Transplantation of Proliferated Human Pre–Islet Cells into Diabetic Patients with Renal Transplants", *Transplantation Proceedings*, 21(1):2751–2756.

*Primary Examiner*—Christina Chan
*Assistant Examiner*—F. Pierre VanderVegt
*Attorney, Agent, or Firm*—Knobbe, Martens, Olson & Bear

[57] ABSTRACT

A method of increasing the number of adult pancreatic islet cells available for transplantation by contacting the cells with laminin 5 extracellular matrix. When contacted with the deposited matrix produced by 804G rat bladder carcinoma cells, a 1,500 fold increase in cell number is observed after three passages in culture. Islet cell expansion also occurs when cells are contacted with 804G soluble matrix. The expanded islet cells contain insulin and respond to glucose challenge.

21 Claims, 6 Drawing Sheets

5,681,587

1

GROWTH OF ADULT PANCREATIC ISLET CELLS

CROSS-REFERENCE TO RELATED APPLICATIONS

This application claims priority to U.S. Provisional application Ser. No. 60/004,878, filed Oct. 6, 1995.

FIELD OF THE INVENTION

The present invention relates to the enhanced growth of adult pancreatic islet cells when cultured in contact with laminin 5.

BACKGROUND OF THE INVENTION

Nearly two million Americans are afflicted with Type I (insulin-dependent) diabetes, in which the pancreas has lost its ability to secrete insulin due to an autoimmune disorder in which the insulin-secreting beta cells, found within the islet cells of the pancreas, are destroyed. Although insulin injections can compensate for beta cell destruction, blood sugar levels can still fluctuate dramatically. The impaired ability to take up glucose from the blood results in side reactions in which toxic products accumulate, leading to complications including blindness, kidney disease, nerve damage, and, ultimately, coma and death.

Researchers have tried smaller, more frequent doses of insulin and mechanical pumps which mimic the action of the pancreas, but the results have been far from ideal. Another option, pancreatic transplant, requires major surgery and is fraught with complications. In addition, the limited availability of donor pancreases leaves a significant number of diabetics without hope for transplantation.

The most promising option thus far is islet cell transplantation using tissue derived from either cadavers or human fetuses. This procedure has been moderately successful. Among the transplants from cadavers performed worldwide, the transplanted tissue survived for a full year in about 20% of recipients. Ten of these recipients are now insulin-independent, while others have a greatly reduced need for insulin. The main problems associated with islet cell transplantation include rejection by the immune system and the causative autoimmune disorder itself which, if left unchecked, will also destroy the transplanted islet cells. In addition, adequate expansion of adult pancreatic islet cells in culture has not been attained.

Fetal pancreatic tissue has also been used as a source of islet cells (Voss et al.,*Transplantation Proc.*, 21: 2751–2756, 1989). Earlier attempts at culturing pancreatic islet cells were complicated by fibroblast contamination (Leach et al., *J. Endocrinol.*, 59: 65–79, 1973). Although partially digested fetal pancreas has been used to produce pancreatic islet-like cell clusters (ICCs), the clinical use of these clusters is limited because only 100–200 can be obtained per pancreas (Sandler et al., *Diabetes*, 34: 1113–1119, 1985; Otonkoski et al., *Acta. Endocrinol.*, 118: 68–76, 1988). Kover and Moore (*Diabetes*, 38: 917–924, 1989) obtained 200–300 islets from a 17 week fetal pancreas, still not enough to be clinically useful. Finally, Simpson et al. (*Diabetes*, 40: 800–808, 1991) generated insulin-secreting, fibroblast-free monolayers of human fetal pancreas plated on bovine corneal matrix (BCM), although adequate numbers of cells for clinical transplantation were not obtained. Although only a small number of cells within the clusters stained positively for the different pancreatic hormones, they differentiated efficiently into mature endocrine cells following transplantation into nude mice (Sandler et al., *Diabetes*, 34: 1113–1119, 1985).

Peck et al. (PCT WO95/29988) cultured pluripotent pancreatic stem cells in vitro. After several weeks, a stromal cell layer was formed. Islet cell differentiation was initiated by refeeding with high amino acid medium supplemented with homologous normal serum containing glucose. After an additional growth period, functional islet cells were recovered by standard techniques.

U.S. Pat. No. 5,541,106, the entire contents of which are hereby incorporated by reference, describes the induction of hemidesmosome formation in epithelial cells cultured thereon by an extracellular matrix produced by the rat bladder carcinoma cell lines 804G and NBT-II. Hemidesmosomes, with their associated structures including intermediate filaments and anchoring fibrils, form an adhesion complex which mediates interaction between epithelial cells and the underlying extracellular matrix.

U.S. Pat. No. 5,422,264, the entire contents of which are hereby incorporated by reference, discloses the culturing of epithelial cells in contact with a soluble 804G matrix equivalent secreted into the culture medium. This 804G soluble matrix contains protein subunits similar to those present in the extracellular matrix deposited by 804G cells as determined by SDS-PAGE and immunological cross reactivity.

U.S. Pat. No. 5,510,263, the entire contents of which are hereby incorporated by reference, describes the growth enhancement of fetal pancreatic islet-like cell clusters cultured in contact with an extracellular matrix secreted by 804G or NBT-II cells.

Human cell matrix molecules structurally similar, if not identical, to the 804G matrix have also been described. Rouselle et al. (*J. Cell Biol.*, 114:567–576, 1991) and Burgeson et al. (PCT WO92/17498; PCT WO94/05316) describe a molecule called kalinin which is secreted into the cell culture medium by human keratinocytes and enhances cell attachment. Carter et al. (*Cell*, 65:599–610, 1991;PCT WO95/06660) describe an epithelial ligand complex called epiligrin found in the extracellular matrix of human keratinocytes. In addition, a 600 kDa basement membrane glycoprotein (BM600) secreted into the culture medium by human keratinocytes (Verrando et al., *Biochim. Biophys. Acta.*, 942:45–56, 1988; Hsi et al., *Placenta* 8:209–217, 1987) comprises protein components similar to those found in the 804G matrix. Although kalinin and epiligrin stimulate cell adhesion, they have not been reported to induce formation of hemidesmosomes.

Thus, there is a need for a simple, reproducible, efficient method of expanding the pool of available pancreatic islet cells for transplantation into diabetic patients. The present invention satisfies this need.

SUMMARY OF THE INVENTION

One embodiment of the present invention is a method of growing adult pancreatic islet-like cell clusters (ICCs), comprising the step of culturing the ICCs in culture media in contact with laminin 5. Preferably, the laminin 5 is the extracellular matrix produced by 804G cells and NBT-II rat bladder carcinoma cells, and the matrix comprises three polypeptides having molecular weights of about 150 kD, 140 kD and 135 kD, the matrix being characterized as:

(a) promoting enhanced growth of the ICCs in comparison to ICCs grown in the absence of the matrix;

(b) having the ability to promote hemidesmosome formation in epithelial cells cultured thereon;

(c) binding concanavalin; and (d) being bound by polyclonal antibodies generated against the matrix.

Preferably, the ICCs are from a mammal; most preferably, the ICCs are human. According to another aspect of this preferred embodiment, the matrix is deposited by the 804G or NBT-II cells onto a substrate, the 804G or NBT-II cells are removed from the matrix, and the ICCs are grown on the matrix. Advantageously, the matrix is secreted by the 804G or NBT-II cells into the culture media. The method may also comprise purifying the secreted matrix from the culture media. Advantageously, the matrix is produced by 804G rat bladder carcinoma cells. Preferably, the polypeptides are produced from recombinant DNA; most preferably, the recombinant DNA is human. According to another aspect of this preferred embodiment, the laminin 5 is kalinin or epiligrin. Alternatively, the laminin 5 is the extracellular matrix produced by MCF 10A cells.

The present invention also provides pancreatic ICCs prepared as described above. Preferably, the growing step expands the cells at least 10 fold, more preferably at least 100 fold. Advantageously, the growing step comprises passaging the ICCs at least two times, and obtaining functional insulin-producing passaged cells.

Another embodiment of the present invention is a method of treating Type I diabetes in a patient in need thereof, comprising the step of administering to the patient an effective insulin-producing amount of pancreatic ICCs prepared as described above. Preferably, the administering step is by implantation under the kidney capsule. Alternatively, the ICCs are placed in an immunoprotective barrier prior to the implantation step. Alternatively, the administering step is by direct injection into the liver. Advantageously, the effective insulin-producing amount is between about $2 \times 10^5$ and about $8 \times 10^5$ ICCs.

DETAILED DESCRIPTION OF THE INVENTION

Figure 1:
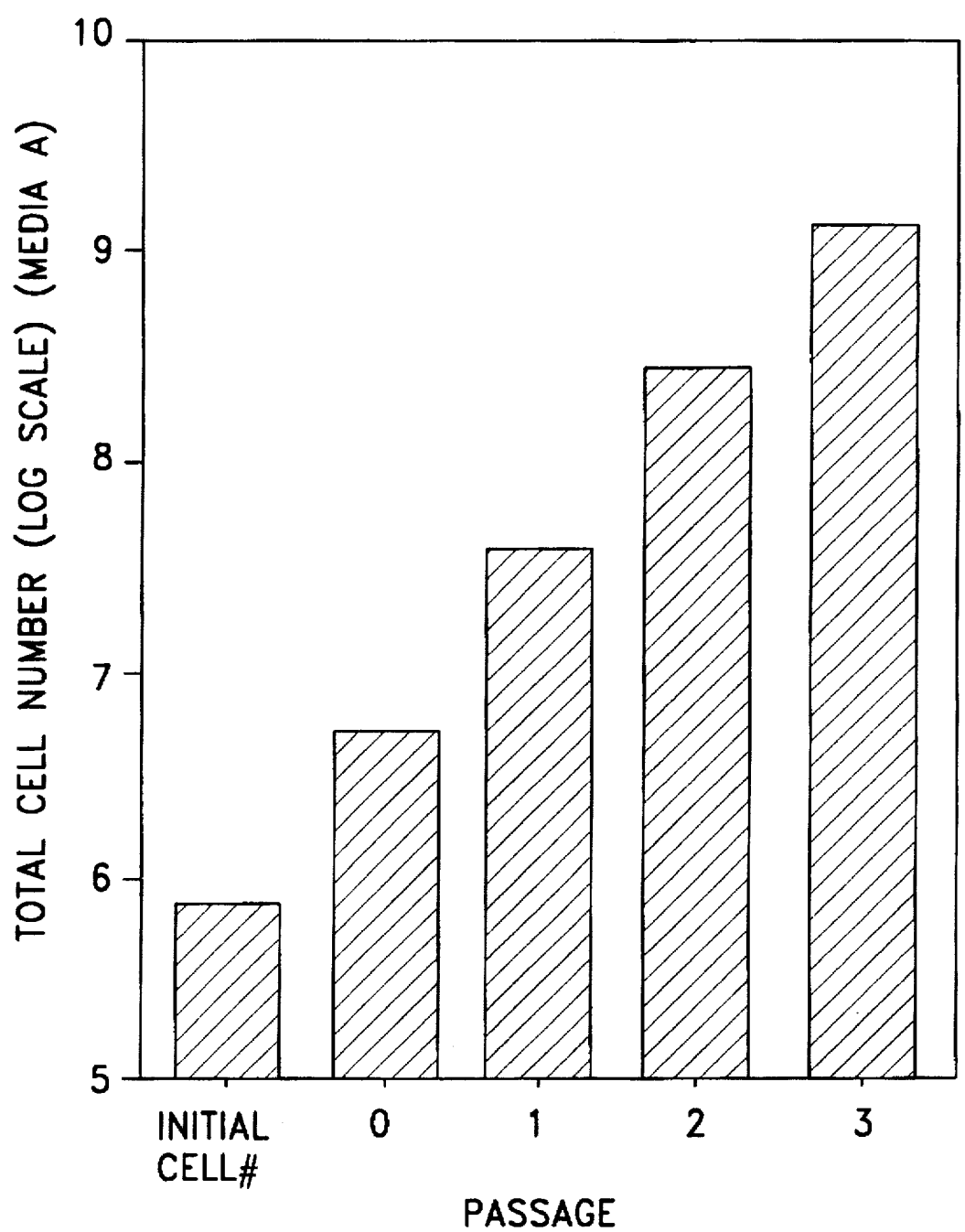
FIG. 1 illustrates the expansion of adult pig islet cells by culturing on the extracellular matrix deposited by 804G cells. The initial number of cells seeded was about $7 \times 10^5$ and was expanded to about $1.46 \times 10^9$ by passage 3. The passage number is shown on the x-axis and the total cell number is shown on the y-axis.

The present invention includes the discovery that certain cell lines produce an extracellular matrix that is capable of stimulating growth of adult pancreatic islet cells cultured thereon. One such cell line is the rat bladder carcinoma cell line 804G. This cell line is described by Izumi, et al., *Cancer Res.* (1981); 41:405–409, and is maintained as a Budapest Treaty patent deposit with the American Type Culture Collection (ATCC), 12301 Parklawn Drive, Rockville, MD., under accession number ATCC 11555, made Feb. 24, 1994. Another such cell line is the rat bladder carcinoma cell line NBT-II which is maintained as a Budapest Treaty patent deposit with ATCC under accession number ATCC 11556 made Feb. 24, 1994. All restrictions on the availability to the public of the deposited cells will be irrevocably removed upon the granting of a patent. The MCF 10A cell line is available from ATCC (ATCC CRL 10317).

It should be noted that the term "laminin 5" is used herein to refer to the preferred cell matrix deposited onto a substrate or secreted into the culture medium by 804G or NBT-II rat bladder carcinoma cells, as well as the structurally related human molecules kalinin (Rouselle et al., *J. Cell Biol.*, 114:567–576, 1991; PCT W092/17498; PCT W094/05316), epiligrin (Carter et al., *Cell*, 65:599–610, 1991; PCT W095/06660), BM600 (Verrando et al., *Biochim. Biophys. Acta*, 942:45–56, 1988; Hsi et al., *Placenta*, 8:209–217, 1987) and the laminin-like 804G matrix equivalent produced by the human MCF 10A mammary epithelial cell line. This cell line is described by Soule et al. (*Cancer Res.*, 50:6075–6086, 1990) and Tait et al. (*Cancer Res*, 50:6087–6094, 1991). The term "laminin 5" is used to generically refer to any of the 804G-related cell matrix molecules described above.

As described in U.S. Pat. No. 5,541,106, ultrastructural data have been developed demonstrating that the 804G matrix is capable of inducing a number of cells to develop mature hemidesmosomes and attach to their growth substrate. Further, it has been discovered that the 804G extracellular matrix contains laminin-like molecules that participate in hemidesmosome assembly. Three of these molecules have been cloned from a rat 804G cDNA library and encode proteins having molecular weights of approximately 150, 140 and 135 kDa.

Thus, the extracellular matrix produced by such cells as 804G and NBT-II cells can modulate the organization of hemidesmosomal antigens in unrelated cells maintained upon it. This effect appears specific to hemidesmosomal elements since adhesion plaque components do not obviously change their localization in cells maintained upon the matrix of the present invention.

The expansion of adult pancreatic islet cells either in vitro or in vivo has not been previously demonstrated. Although methods related to expansion of adult pancreatic islet cells by culturing on the 804G cell matrix are specifically disclosed, it can be appreciated that any cell matrix having the ability to support pancreatic islet cell expansion thereon is within the scope of the present invention, regardless of its ability to stimulate hemidesmosome formation. Such matrices include kalinin, epiligrin, MCF 10A matrix and BM600. Because the extracellular matrix secreted by both 804G and NBT-II cells contain similar protein components as determined by immunoblotting experiments, the NBT-II matrix will also support the expansion of mature pancreatic islet cells cultured thereon.

A 1,500 fold expansion of adult pig pancreatic islet cells cultured on 804G matrix was obtained after three passages in culture. It should be noted that the term "adult pancreatic islet cells" refers to those fully differentiated pancreatic cells capable of secreting insulin. As defined herein, "804G matrix" comprises one or more protein components deposited by 804G rat bladder carcinoma cells which facilitates growth of pancreatic islet cells cultured in contact with the matrix. The use of the structurally similar molecules kalinin, epiligrin, MCF 10A matrix and BM600 is also within the scope of the present invention. The term "804G soluble matrix" refers to the hemidesmosome induction-facilitating soluble matrix equivalent secreted by 804G cells into the culture medium. Structurally equivalent soluble matrix molecules include kalinin and the soluble matrix secreted by MCF 10A cells.

The 804G soluble matrix (95% purity; DESMOS, Inc., San Diego, Calif.) also stimulated growth of adult pig islets cultured on soluble matrix-coated tissue culture plastic as assessed by an increase in intracellular DNA content. This purified soluble matrix was purified by conventional protein purification techniques known to one of ordinary skill in the art. Further, the expanded islet cells released insulin in response to a glucose challenge and exhibited an increase in intracellular insulin content. The optimal dilution of the 95% pure material was 1:30. The skilled artisan will appreciate that any dilution may be tested for the ability to support islet cell expansion as described in Example 3.

The 804G matrix also promoted enhanced growth of pancreatic islet cells cultured thereon. After one passage in culture, a significant increase in the number of adult islets was obtained, similar to that observed with the expanded pig islets after one passage in culture.

A substrate upon which pancreatic islet cells are to be grown is coated with the matrix deposited by or soluble matrix secreted by 804G cells or with any of the other structurally and functionally similar molecules described herein. The 804G matrix is prepared as described in U.S. Pat. No. 5,541,106. Soluble 804G matrix is described in U.S. Pat. No. 5,422,264. Kalinin and epiligrin are present in the conditioned medium of human keratinocytes. The conditioned medium itself may be used as a source of kalinin and epiligrin. Kalinin may be immunopurified from conditioned medium using an immunoaffinity column directed against its BM165 antigen (Rousselle et al., *J. Cell Biol.*, 125:205–214, 1994). Epiligrin is also present in the cell matrix secreted by human keratinocytes and may be isolated by a three-step extraction procedure comprising 1% w/v TRITON X-100® to solubilize membrane and cytoplasmic components; 2M urea and 1M NaCl to remove nuclear and cytoskeletal components; and 8M urea to solubilize residual components. 0.5% (w/v) sodium dodecyl sulfate (SDS) is then added and the matrix removed by scraping (Carter et al., *Cell*, 65:599–610, 1991; PCT WO95/06660). MCF 10A matrix is prepared as described in Example 1. It will be appreciated that the use of any soluble or insoluble laminin 5 is within the scope of the present invention.

The cells to be grown are then plated on or applied to the matrix-coated substrate using standard tissue culture techniques, followed by passaging in standard cell growth medium. Any medium capable of supporting the enhanced growth of adult islet cells on the matrix-coated substrate is within the scope of the invention. Such cells, including human cells in vitro and in vivo, will grow in an organized fashion on the substrate and will exhibit significantly enhanced growth compared to pancreatic islet cells grown on conventional matrices such as bovine corneal matrix (BCM). It appears that the organization of islet cells growing on the 804G matrix is significantly more advanced and more tissue-like than cells grown in the absence of 804G matrix.

The islet cells can be removed from the original substrate and transferred to several new substrates coated with laminin 5, allowing large-scale expansion of these cells. The cells are tested for their ability to respond to a glucose challenge by measuring the levels of insulin secreted into the culture medium by well known methods. After culturing, the cells can be re-aggregated into three-dimensional structures and either placed into an immunoprotective barrier such as sodium alginate, hollow fibers or polyethylene glycol (Lonza et al., Transplantation, 56:1067–1072, 1993; Iwata et al., *J. Biomed. Materials Res.*, 28:1003–1011, 1994) or directly implanted in vivo for treatment of diabetes. The cells are also analyzed for insulin content by ELISA or radioimmunoassays known to one of ordinary skill in the art.

The substrate on which pancreatic islet cells are grown may be any desired substrate. For laboratory use, the substrate may be as simple as glass or plastic. Alternatively, any suitable substrate may be used, including various shaped articles, fabrics, prosthetic implants, and the like. For use in vivo, the substrate may be any biologically compatible material on which pancreatic islet cells can grow. Suitable substrate materials include shaped articles made of or coated with such materials as collagen; regenerated collagen; polylactic acid; hyaluronic acid; biocompatible metals such as stainless steel and titanium; ceramic materials including prosthetic materials such as hydroxylapatite; synthetic polymers, including polyesters and nylons; biological materials that are actually part of a patient, such as connective tissue and other organs, and virtually any other material to which biological molecules can readily adhere.

Pancreatic islet cells may be grown in vitro in the presence of laminin 5 for transplantation into diabetic patients. Growth of pancreatic islet cells in the presence of laminin 5 increases the yield of islet cells for transplantation and thus solves the long felt but unsolved need of producing larger amounts of these cells. The use of any "804G matrix" protein as a substrate for the growth of pancreatic islet cells is advantageously envisioned, including all proteins secreted by cell lines which are capable of enhancing the growth of pancreatic islet cells. In addition, it is contemplated that the inclusion of one or more growth factors in the adult islet cell culture medium will further increase the yield of islet cells.

The resulting islet cells are fully functional after transplantation into mammals, preferably humans, and will reduce or eliminate the need for insulin injections. The fold increase in the number of adult pig islet cells after culturing on 804G matrix for three passages is about 1500, which may be sufficient for transplantation into a diabetic patient. It is envisioned that after routine optimization of the growth conditions, an even greater increase can be obtained.

The 804G matrix of the present invention comprises three concanavalin-binding glycosylated proteins, of approximately 135 kD, 140 kD and 150 kD, all of which are recognized by polyclonal antibodies generated against the 804G matrix. The methods of the present invention may be practiced with the complete, active matrix from 804G cells or a functionally equivalent "804G" matrix from other cells, and may also be practiced with any one of the individual protein components of the matrix which promote enhanced islet cell growth. The same statement applies to the individual protein components of any of the other laminin 5 molecules described herein. Cell matrix and matrix proteins can be readily screened for the ability to enhance growth of pancreatic islet cells, using the techniques described herein. Only routine experimentation is required.

In addition to the active molecules and the active components thereof, the present invention also includes shaped articles coated with those materials. Preferably, those shaped articles are formed of materials other than glass, and include such forms as sheets, fabrics, prostheses, metal articles, bioerodible articles, and implantable articles.

The extracellular matrix may be harvested (as by scraping, abrading, or treatment with low concentrations of SDS) from surfaces on which appropriate matrix-depositing cells have been grown. Alternatively, the matrix materials may be prepared synthetically or through recombinant DNA techniques using, for example, murine or human cDNA libraries, or through purification of deposited matrix material. The extracellular matrix may also be isolated in soluble form by harvesting the conditioned medium from 804G, NBT-II, MCF 10A or human keratinocytes which is may be used to coat substrates on which the islet cells are cultured. Moreover, the particular molecule of interest may be purified from conditioned medium and used to coat the substrate. The extracellular matrix deposited by the cell lines may also be used after removal of the cells, without further processing or purification. In this embodiment, islet cells are cultured on the deposited matrix after removal of cells by treatment with, for example, low concentrations of ammonium hydroxide as described for 804G cells in U.S. Pat. No. 5,541,106.

Soluble and insoluble laminin 5 are isolated from MCF 10A cells as described in the following example.

EXAMPLE 1

Isolation of Laminin 5 from MCF 10A Cells

The insoluble matrix was prepared from five day old MCF 10A cultures as described for 804G cells in U.S. Pat. No. 5,541,106. Briefly, cell monolayers were washed in phosphate buffered saline (PBS), then treated for about five minutes with 20 mM $NH_4OH$. Cell remnants were washed from the substrate with PBS.

EXAMPLE 2

Expansion of Pancreatic Islet Cells on 804G Matrix in vitro

Adult pig primary islet cells containing approximately 2,000 cells per islet (Neocrin, Irvine, Calif.) were seeded onto tissue culture plastic coated with extracellular matrix deposited by 804G cells. Briefly, 804G cells were removed from the plates with 20 mM ammonium hydroxide, leaving deposited 804G matrix on the substrate. Islet cells were seeded into six-well tissue culture plates containing the deposited matrix in RPMI medium containing 10% fetal bovine serum (FBS). Approximately 50 islets were allowed to attach to one well of a six-well plate and the cells began to expand from the islet cluster within 24 hours. By seven to ten days post-seeding, the cells had reached confluence and were then removed with 0.05% trypsin and either passed to several surfaces or assayed in situ for glucose responsiveness and cellular insulin content.

As seen in FIG. 1, the total cell number increased significantly when cultured and passaged on 804G matrix (about 1500 fold).

EXAMPLE 3

Expansion of Islet Cells Using 804G Soluble Matrix

Adult pig islets were seeded onto tissue culture plastic coated with different concentrations of 804G soluble matrix (approximately 95% pure as detected by densitometry of a Coomassie blue-stained SDS gel). Primary islet cells were seeded in six well tissue culture plastic plates at 50 islets per well in RPMI containing 10% FBS. In three wells, 804G cells were grown to confluence and the cells were removed using ammonium hydroxide, leaving the deposited matrix in the wells. Three wells were coated with a 1:10, 1:30, 1:90, 1:270 and 1:810 dilution of the 95% pure protein (15 wells total, three per dilution). Three wells were coated with FBS and three were coated with a crude SEPHADEX™ G-25 (Pharmacia, Piscataway, N.J.) column fraction of 804G cell conditioned medium.

The 95% pure soluble matrix was provided frozen in a volume of 250 μL. Prior to thawing and just prior to use, 12.5 μl FBS and 12.5 μl sterile 100 mM (N-[2-Hydroxyethyl] piperazine-N'-[2-ethanesulfonic acid]) (HEPES) (pH 6.9) was added to the protein. The wells were coated with one ml diluent overnight at 4° C., then washed with PBS. At day 10 of the culture period, the media was changed to a low glucose media (100 mg/dL) for three days.

Figure 2:
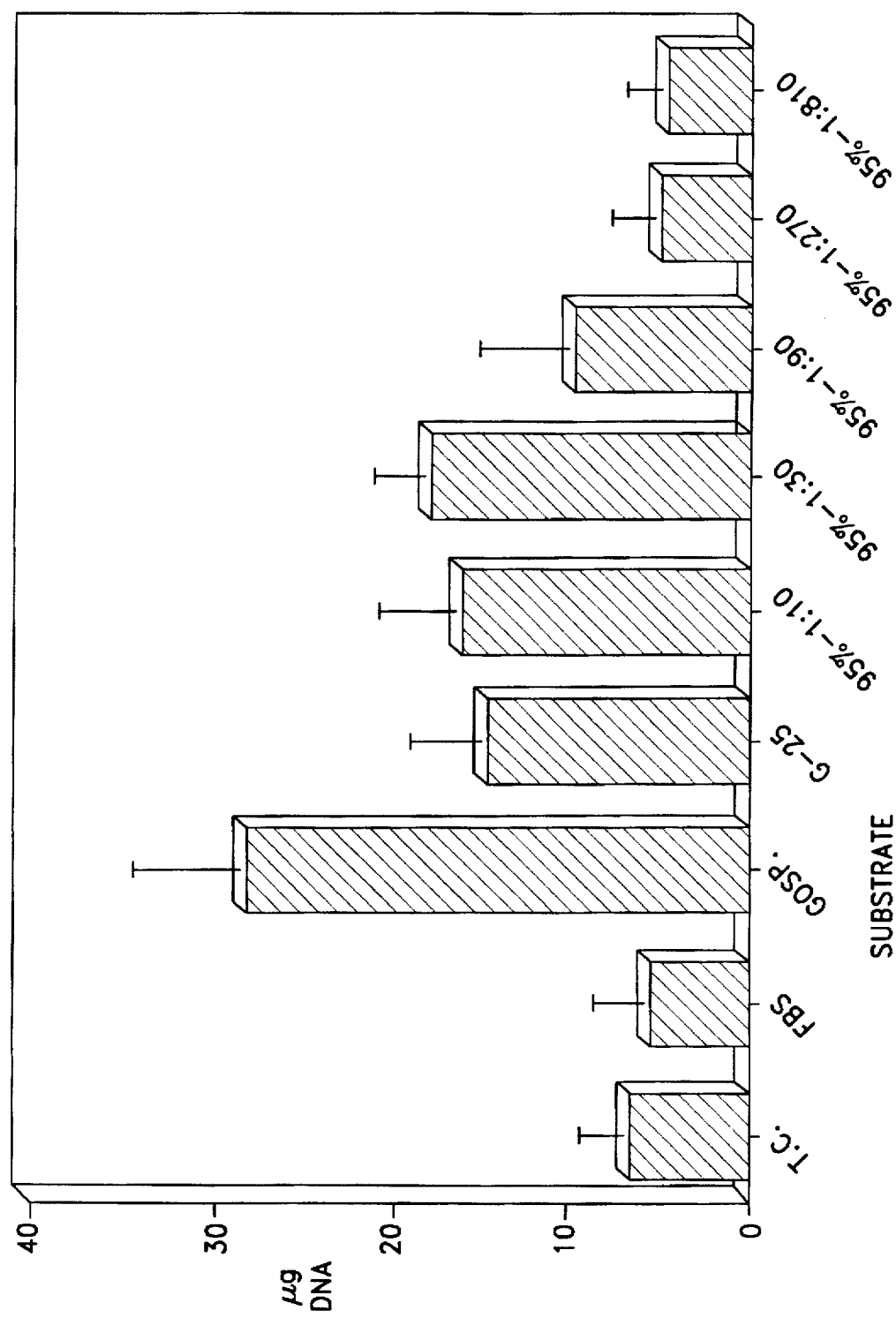
FIG. 2 shows the expansion of adult pig islet cells on various substrates. T.C., FBS and Gosp. correspond to tissue culture plastic, tissue culture plastic pre-coated with fetal bovine serum and solubilized deposited 804G matrix. G-25 is a crude soluble preparation of soluble 804G matrix. Dilutions of the 95% pure protein are shown as 1:30, 1:90, 1:270 and 1:810.

On day 13 the monolayer cultures were assayed for intracellular insulin and DNA content by using the protocol described in Example 5. Cell growth was assessed by increased intracellular DNA content. The results are summarized in FIG. 2. The 804G matrix (Gosp.) resulted in the highest intracellular DNA content. The optimal dilution of 95% pure protein for islet cell expansion was 1:30. This dilution was chosen for the glucose challenge and intracellular insulin content experiments described in Examples 5 and 6 below.

It is also contemplated that the soluble protein may be used as a media supplement and added to the culture upon seeding of the cells.

EXAMPLE 4

Expansion of Islet Cells Using Other Laminin 5 Molecules

The procedure of Example 2 is repeated, except that the cells are grown in the presence of either MCF 10A deposited matrix, MCF 10A soluble matrix, epiligrin or kalinin. Comparable results are obtained.

EXAMPLE 5

Glucose Responsiveness of Expanded Islet Cells

Glucose responsiveness of the islet cells expanded on 804G matrix and 804G soluble factor was determined per unit DNA in response to a glucose/theophylline static challenge. Cells were incubated in a low glucose medium (100 mg/dl–RPMI +2% serum) for at least three days prior to a glucose challenge. The cells were then incubated for 30 minutes in either a resting concentration of glucose (50 mg/dl) or stimulated with 325 mg/dl glucose plus 10 mM theophylline. Cells were collected from the dish, sonicated and processed as described below.

Figure 3:
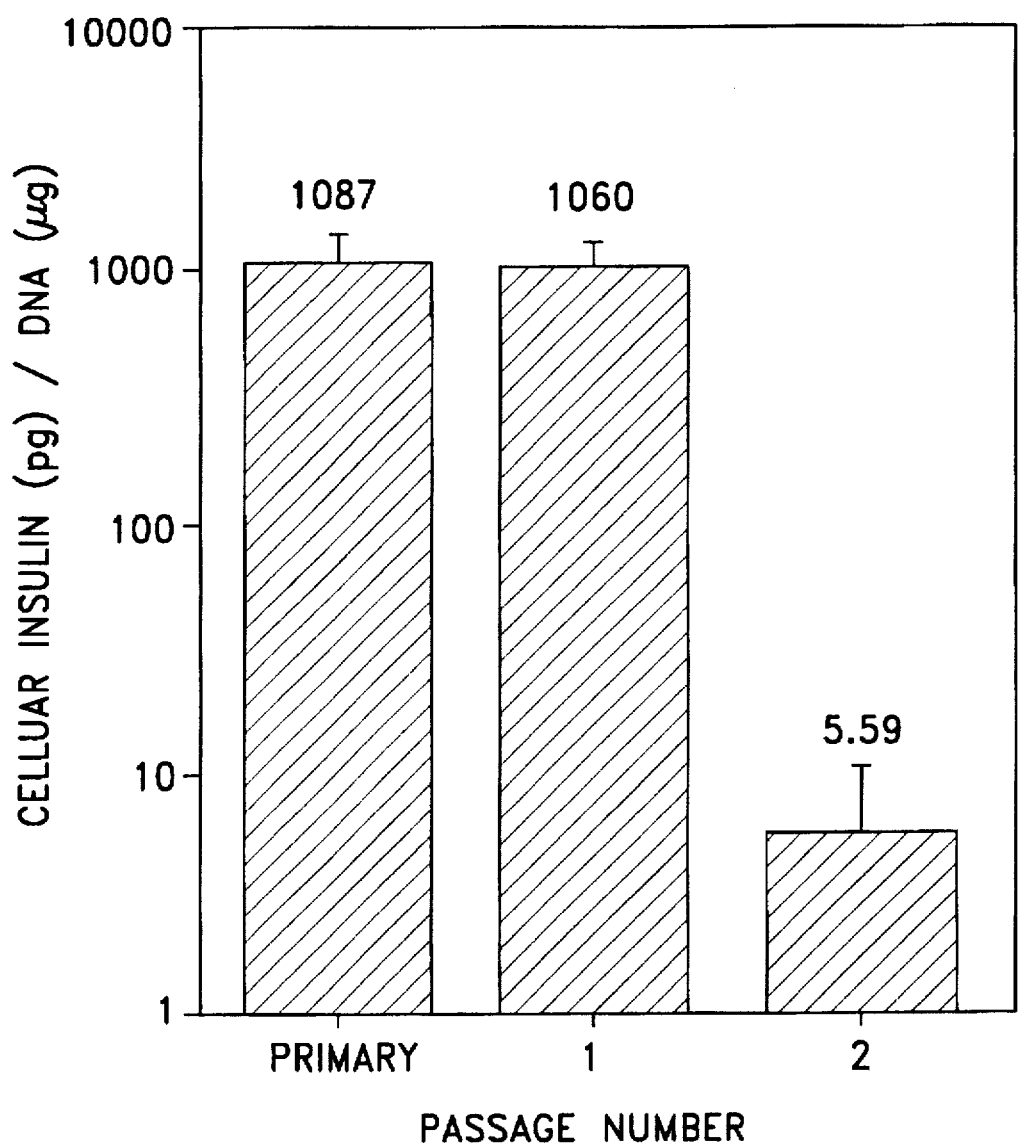
FIG. 3 shows the glucose response of adult pig islets passaged once or twice on 804G extracellular matrix.
Figure 4:
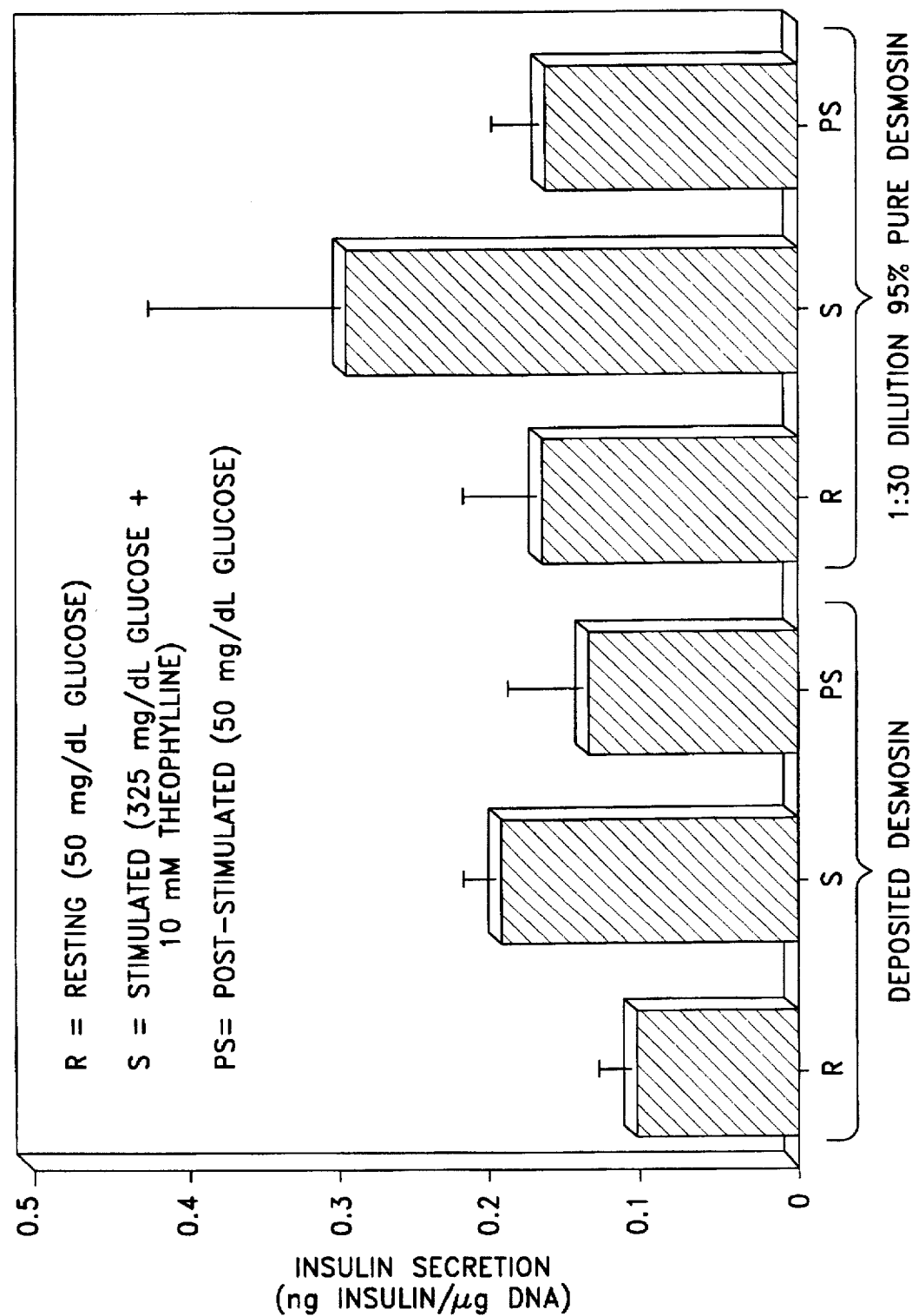
FIG. 4 shows the glucose response of adult pig islet cells grown on both deposited 804G matrix and tissue culture plastic coated with soluble 804G matrix.

FIGS. 3 and 4 show that the cells expanded on both the 804G matrix and 804G soluble factor, respectively, respond to a glucose challenge by secreting insulin into the cell culture supernatant and upon removal of the stimulation, revert to a lower insulin secretion level. The islet cells expanded on soluble matrix exhibited a greater level of insulin secretion than cells expanded on deposited matrix.

EXAMPLE 6

Determination of Intracellular Insulin Content

Figure 5:
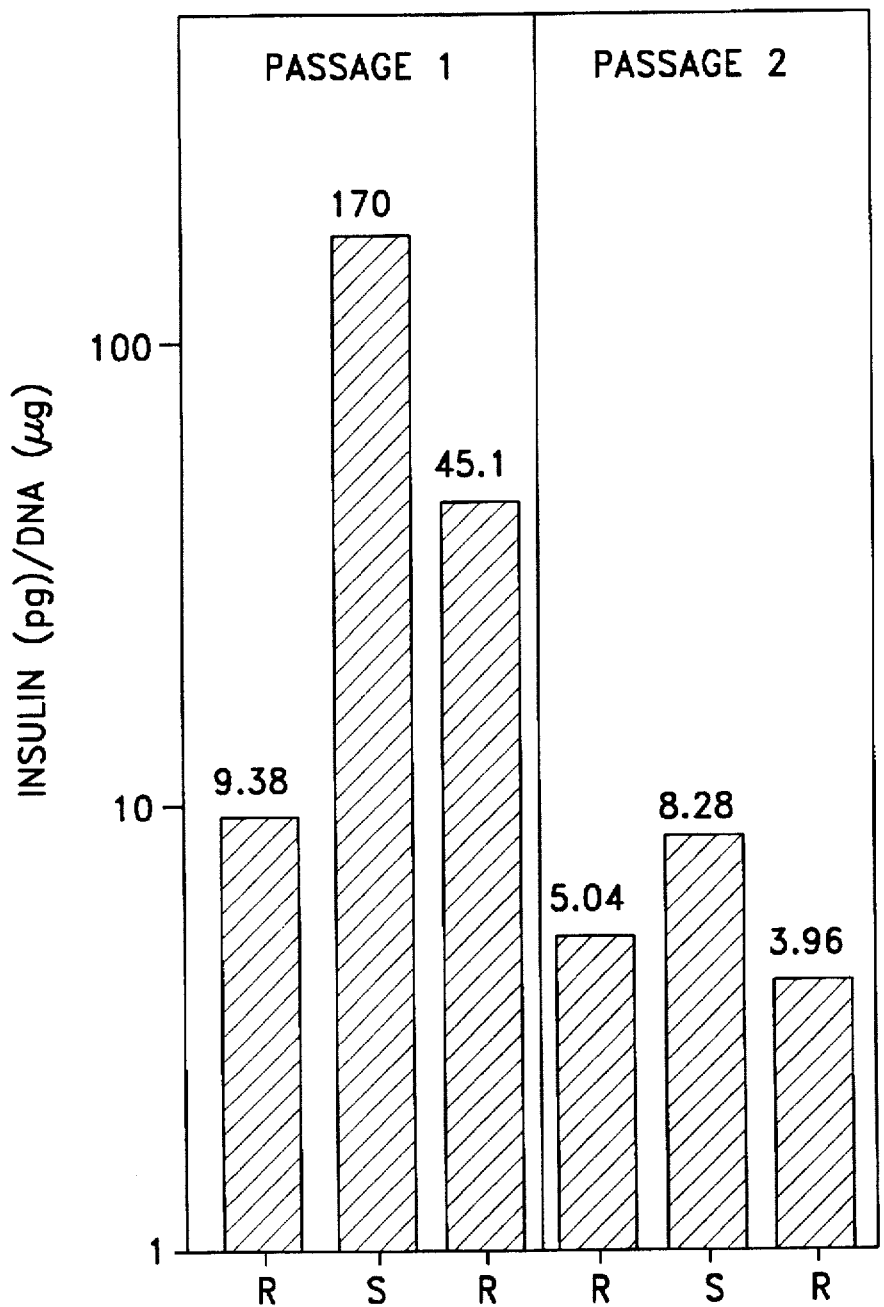
FIG. 5 illustrates the cellular insulin content measured by an ELISA for primary adult pig islet cells and for pig islets expanded by culturing on 804G extracellular matrix. The passage number is shown on the x-axis and the cellular insulin content is shown on the y-axis.
Figure 6:
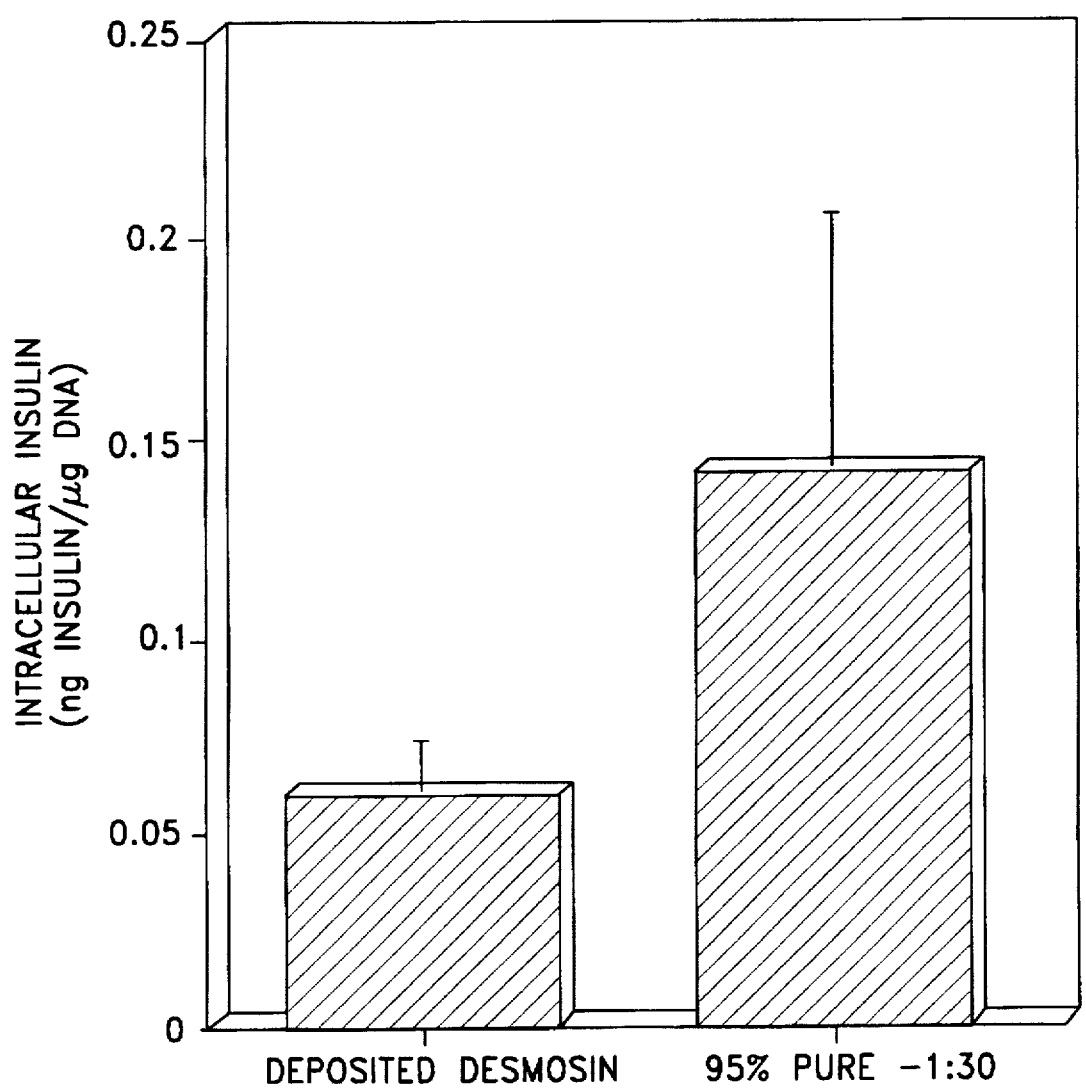
FIG. 6 shows the intracellular insulin content of adult pig islets grown on both deposited 804G matrix and tissue culture plastic coated with soluble 804G matrix.

Intracellular insulin content was determined and expressed as a ratio of cellular insulin/DNA (FIGS. 5 and 6).

After glucose responsiveness determination, plated cells were washed once with PBS and then with 1 ml water per well was added. The wells containing the attached cells were frozen at −20° C. Plates were thawed and cells were removed by mechanical scraping. For islet-like cell clusters or reaggregated cells, the concentration is 100 ICCs/ml. The cells were sonicated at setting number 3 on a Fisher Scientific 60 Dismembrator for 10 seconds or until no particulate matter as observed by gross visual inspection. The samples were then stored at −20° C. until performing an insulin ELISA using a kit from Peninsula Laboratories, Belmont, Calif. FIG. 5 illustrates that culturing on 804G matrix, after 1 passage in culture, does not affect the cellular insulin content compared to primary adult pig islet cells not plated on 804G matrix. FIG. 6 shows that a 1:30 dilution of the 95% pure soluble protein increased intracellular insulin content three fold compared to deposited 804G matrix.

DNA content was determined using a fluorometric dye (Hoechst 33258, American Hoechst Co.). A working solution of the dye was prepared immediately before use by diluting a 1.0 mg/ml stock solution of dye 2000 fold in dye dilution buffer (10 mM Tris HCl, pH 7.4, 1 mM EDTA, 0.1 mM NaCl) to yield a dye concentration of 0.5 µg/ml. A standard solution of calf thymus DNA (100 µg/ml) was prepared and diluted to obtain standard solutions ranging from 0 µg/ml to 15 µg/ml. The assay was formatted to individual fluorometer cuvettes per sample. A Turner Model 450 fluorometer was set at an excitation wavelength to 360 nm, an emission wavelength of 450 nm, and a 7 mm light aperture. Two ml dye solution was added to each cuvette followed by addition of 250 µl of standard or sample solution. The samples were incubated at room temperature for 30–45 min in the dark, and then read on a fluorometer at 360 nm and 450 nm. The DNA content in the samples was determined by fitting the fluorescent unit value obtained for each sample against the standard curve slope of fluorescent units versus concentration.

EXAMPLE 7

Expansion of Adult Human Pancreatic Islet Cells on 804G Matrix

Adult human pancreas from a cadaver was obtained from the VA hospital, Los Angeles, Calif. The islet cells were isolated by homogenization and collagenase treatment, methods well known in the art (Otonkoski et al., *Acta Endocrinol.*, 118:68–76, 1988). The islet cells were plated on 804G matrix or a 1:30 dilution of the 95% pure soluble 804G matrix and expanded as described in Example 2, then passaged once in culture. A significant increase in the number of adult islets is obtained, similar to that observed with the expanded pig islets after one passage in culture. The expanded human islets are fully functional as determined by insulin content and response to glucose challenge.

EXAMPLE 8

Expansion of Adult Human Pancreatic Islet Cells on Laminin 5

Similar results are obtained when MCF 10A soluble or insoluble matrix, epiligrin or kalinin is used in place of 804G matrix.

EXAMPLE 9

Transplantation of Islet Cells into Nude Mice

Expanded pancreatic islet cells obtained by the method described in Examples 2, 3 or 4 are transplanted under the kidney capsule of athymic nude mice with approximately $6 \times 10^6$ cells or approximately $3 \times 10^3$ ICCs and the grafts are analyzed after 3 months. An increased level of human C-peptide, released into the blood after processing of the insulin precursor molecule, is detected in the blood of grafted animals by the well-known method of radioimmunoassay after an intraperitoneal glucose challenge indicating that the grafted cells are able to produce insulin. In addition, immunocytochemistry of graft cells using an antibody to insulin yields positive results indicating that the islet cells are functional.

EXAMPLE 10

Transplantation of Islet Cells into Diabetic Patients

Human Type I diabetic patients are administered approximately $2-8 \times 10^5$ adult-derived pancreatic islet cells prepared in accordance with Examples 2, 3 or 4, by encapsulating the cells in an immunoprotective barrier and then implanting under the kidney capsule, by implantation under the kidney capsule or by direct injection into the liver. In addition, transplantation in other ectopic organ locations is also contemplated. C-peptide production and blood glucose levels are monitored over several months to determine whether transplanted islet cells are producing insulin. The patients are still administered insulin during the monitoring period.

What is claimed is:

1. A method of expanding adult pancreatic islet-like cell clusters (ICCs), comprising the steps of:
   culturing said ICCs in contact with laminin 5; and
   passaging said cultured ICCs in contact with laminin 5 at least once, whereby the number of said cultured ICCs is significantly increased after said passaging.

2. The method of claim 1, wherein said laminin 5 is the extracellular matrix produced by 804G, ATCC 11555 or NBT-II, ATCC 11556, rat bladder carcinoma cells, said matrix comprising three polypeptides having molecular weights of about 150 kD, 140 kD and 135 kD, said matrix characterized as:
   (a) promoting enhanced growth of said ICCs in comparison to ICCs grown in the absence of the matrix;
   (b) having the ability to promote hemidesmosome formation in epithelial cells cultured thereon;
   (c) binding concanavalin; and
   (d) being bound by polyclonal antibodies generated against the matrix.

3. The method of claim 1, wherein said ICCs are from a mammal.

4. The method of claim 3, wherein said ICCs are from a human.

5. The method of claim 2, wherein said laminin 5 is deposited by said 804G, ATCC 11555 or said NBT-II, ATCC 11556, cells onto a substrate, said cells are removed from said matrix, and said ICCs are grown in contact with said matrix.

6. The method of claim 2, wherein said matrix is secreted by said 804G, ATCC 11555 or said NBT-II, ATCC 11556, cells into said culture media.

7. The method of claim 6, further comprising purifying said secreted laminin 5 from said culture media.

8. The method of claim 2, wherein said laminin 5 is produced by 804G, ATCC 11555, cells.

9. The method of claim 2, wherein said polypeptides are produced from recombinant DNA.

10. The method of claim 9, wherein said recombinant DNA is human.

11. The method of claim 1, wherein said laminin 5 is selected from the group consisting of kalinin and epiligrin.

12. The method of claim 1, wherein said laminin 5 is MCF 10A, ATCC CRL-10317, matrix.

13. The pancreatic ICCs prepared in accordance with claim 1.

14. The method of claim 1, wherein said ICCs are expanded at least 10 fold.

15. The method of claim 1, wherein said ICCs are expanded at least 100 fold.

16. The method of claim 1, wherein said ICCs in contact with laminin 5 are passaged at least twice, and obtaining functional insulin-producing passaged cells.

17. A method of treating Type I diabetes in a patient in need thereof, comprising the step of administering to said patient an effective insulin-producing amount of the ICCs of claim 13.

18. The method of claim 17, wherein said administering step is by implantation under the kidney capsule.

19. The method of claim 18, wherein said ICCs are placed in an immunoprotective barrier prior to said implantation.

20. The method of claim 17, wherein said administering step is by direct injection into the liver.

21. The method of claim 17, wherein said effective insulin-producing amount is between about $2\times10^5$ and about $8\times10^5$ ICCs.

* * * * *